(12) United States Patent  
Moulder et al.

(10) Patent No.: US 8,099,173 B2  
(45) Date of Patent: Jan. 17, 2012

(54) IMPLANTABLE MEDICAL LEAD CIRCUITRY AND METHODS FOR REDUCING HEATING AND/OR INDUCED CURRENT

(75) Inventors: J. Christopher Moulder, Portland, OR (US); Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 388 days.

(21) Appl. No.: 12/393,972

(22) Filed: Feb. 26, 2009

(65) Prior Publication Data

US 2010/0217366 A1 Aug. 26, 2010

(51) Int. Cl.  
*A61N 1/00* (2006.01)
(52) U.S. Cl. ........................................... 607/119
(58) Field of Classification Search .................... 607/119  
See application file for complete search history.

(56) References Cited

U.S. PATENT DOCUMENTS

| 5,030,862 | A | * | 7/1991 | Prentice | .......................... | 327/441 |
| 5,968,083 | A | * | 10/1999 | Ciciarelli et al. | ............... | 607/62 |
| 7,363,090 | B2 | | 4/2008 | Halperin et al. | | |
| 2007/0255332 | A1 | | 11/2007 | Cabelka et al. | | |
| 2008/0058902 | A1 | * | 3/2008 | Gray et al. | ....................... | 607/59 |

FOREIGN PATENT DOCUMENTS

WO 2005030320 A1 4/2005  
WO 2007127705 A1 11/2007

* cited by examiner

*Primary Examiner* — George Manuel

(57) ABSTRACT

An implantable medical lead for coupling to an implantable pulse generator may be configured for improved safety. The lead may include: a first electrode; a second electrode in electrical communication with the first electrode; and an active circuit element in electrical communication with the first electrode and the second electrode. The active circuit element may be configured to change an impedance of the lead. The active circuit element may be configured to change the impedance of the lead in response to a pacing signal or a signal having opposite polarity to a pacing signal. A method of using an implantable medical lead for improved safety may include changing an impedance of an implantable medical lead from a relatively high impedance to a relatively low impedance and/or changing an impedance of an implantable medical lead from a relatively low impedance to a relatively high impedance.

19 Claims, 6 Drawing Sheets

IMPLANTABLE MEDICAL LEAD CIRCUITRY AND METHODS FOR REDUCING HEATING AND/OR INDUCED CURRENT

FIELD OF THE INVENTION

The present invention relates to medical methods and apparatus. More specifically, the present invention relates to implantable medical leads and methods of utilizing such leads.

BACKGROUND OF THE INVENTION

Existing implantable medical leads for use with implantable pulse generators, such as neurostimulator, pacemakers, defibrillators or implantable cardioverter defibrillators ("ICD"), are prone to heating and induced current when placed in the strong magnetic (static, gradient and RF) fields of a magnetic resonance imaging ("MRI") machine. The heating and induced current are the result of the lead acting like an antenna in the magnetic fields generated during an MRI. Heating and induced current in the lead may result in deterioration of stimulation thresholds or, in the context of a cardiac lead, even increase the risk of cardiac tissue damage and perforation. Moreover, induced currents may cause erroneous pacing or even fibrillation.

Over fifty percent of patients with an implantable pulse generator and implanted lead require, or can benefit from, an MRI in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

There is a need in the art for an implantable medical lead configured for improved MRI safety. There is also a need in the art for methods of using such a lead.

SUMMARY

Disclosed herein is an implantable medical lead for coupling to an implantable pulse generator and configured for improved MRI safety. In particular, embodiments of leads disclosed herein may improve MRI safety by reducing induced currents in medical leads. Such reduction may reduce or even eliminate risks of stimulation and/or heating resulting from exposure of medical leads to magnetic and/or electrical fields.

In one embodiment, the lead may include a first electrode and a second electrode in electrical communication with the first electrode. The lead may include at least one active circuit element in electrical communication with the first and second electrodes. The at least one active circuit element may be configured to change an impedance of the lead, for example, in response to a pacing signal or a signal having opposite polarity to a pacing signal.

Disclosed herein is a method of using an implantable medical lead for improved MRI safety. In particular, embodiments of methods disclosed herein may improve MRI safety by reducing induced currents in medical leads. Such reduction may reduce or even eliminate risks of stimulation and/or heating resulting from exposure of medical leads to magnetic and/or electrical fields.

In one embodiment, the method may include changing an impedance of an implantable medical lead from a relatively high impedance to a relatively low impedance, for example, in response to a pacing signal. In another embodiment, the method may include changing an impedance of an implantable medical lead from a relatively low impedance to a relatively high impedance, for example, in response to a signal having opposite polarity to a pacing signal.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The following description is of embodiments presently contemplated for practicing various aspects of the invention. This description is not to be taken in a limiting sense, but is made merely for the purpose of describing general principles. The scope of the invention should be ascertained with reference to the issued claims. In the description that follows, like numerals or reference designators will be used to refer to like parts or elements throughout.

Embodiments are described herein in relation to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. The stimulation device is intended for use in patients suffering from hemodynamic dysfunction, which may or may not be accompanied by conduction disorders. Precisely controlled stimulation at multiple sites or in multiple chambers is provided to intentionally make use of the pacing function of the heart to improve cardiac hemodynamics by re-coordinating heart chamber contractions and/or preventing arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

The disclosed devices and methods are directed to implantable leads for such implantable devices. However, it should be understood that the disclosed devices and methods may be applicable to implantable leads for other devices as well. Thus, the implantable leads and the methods described herein may be implemented in any cardiac stimulation device or other device in which implantable leads are employed.

Figure 1:
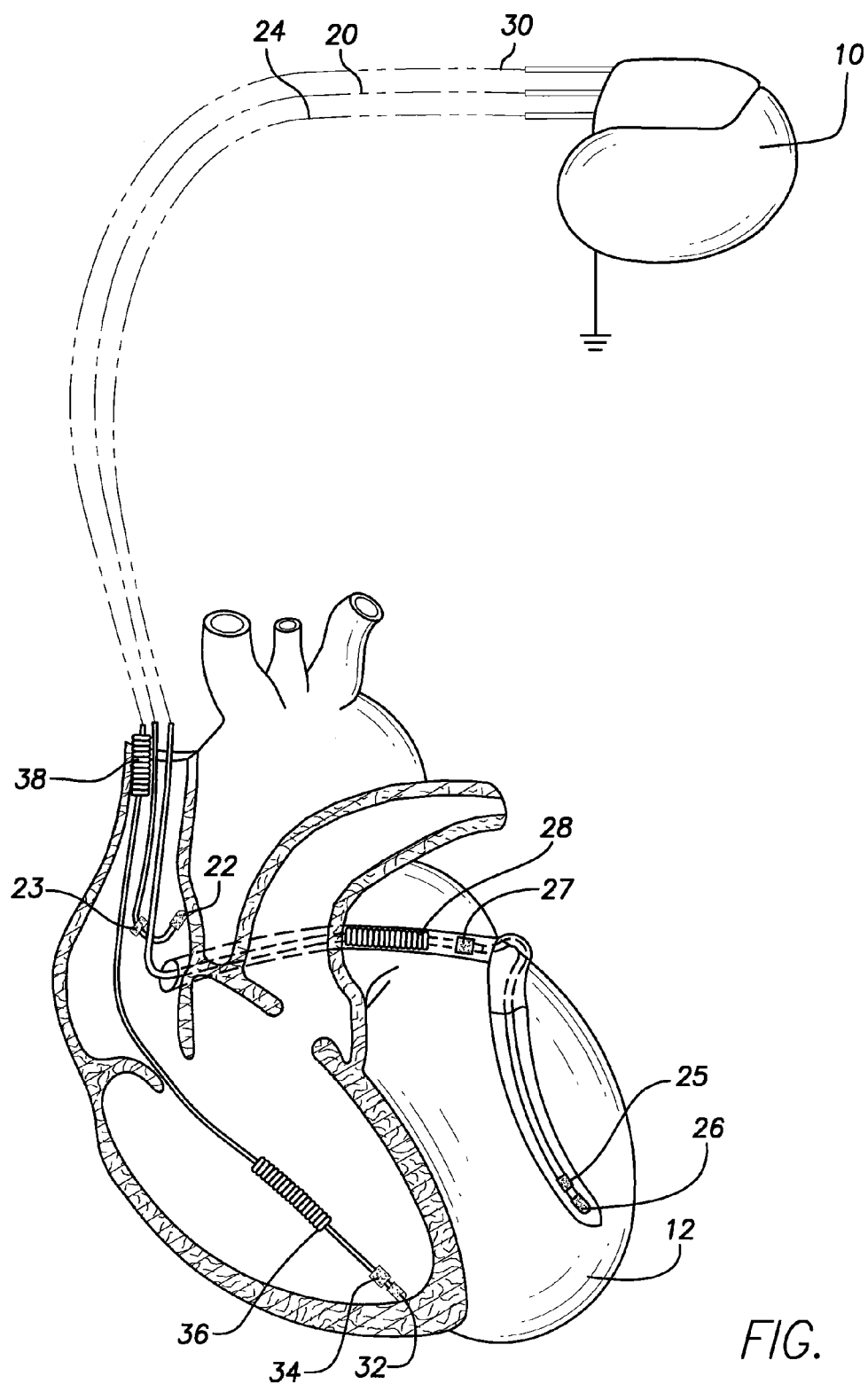
FIG. 1 is a simplified, partly cutaway view of a patient's heart and illustrating an implantable stimulation device in electrical communication with three leads implanted into the heart for delivering multi-chamber stimulation and shock therapy.

A general cardiac stimulation device will thus be described in conjunction with FIG. 1, in which the implantable leads and the methods described herein may be implemented. It should be understood, however, that numerous variations exist of such a device in which the leads and/or methods may be implemented.

FIG. 1 illustrates a stimulation device 10 in electrical communication with a patient's heart 12 by way of three leads 20, 24 and 30 suitable for delivering multi-chamber stimulation and shock therapy. To sense right atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have a right atrial ring electrode 23 to allow bipolar stimulation or sensing in combination with the right atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. In an alternative embodiment, the coronary sinus lead 24 may also include a left ventricular ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As disclosed herein, an implantable medical lead may be configured for improved MRI safety. In various embodiments, the lead may include circuitry configured to reduce, if not totally eliminate, the potential for MRI induced currents and/or heating in the lead, for example, in conductors extending through the lead body to electrodes, such as those used for pacing, sensing and/or defibrillation.

Figure 2:
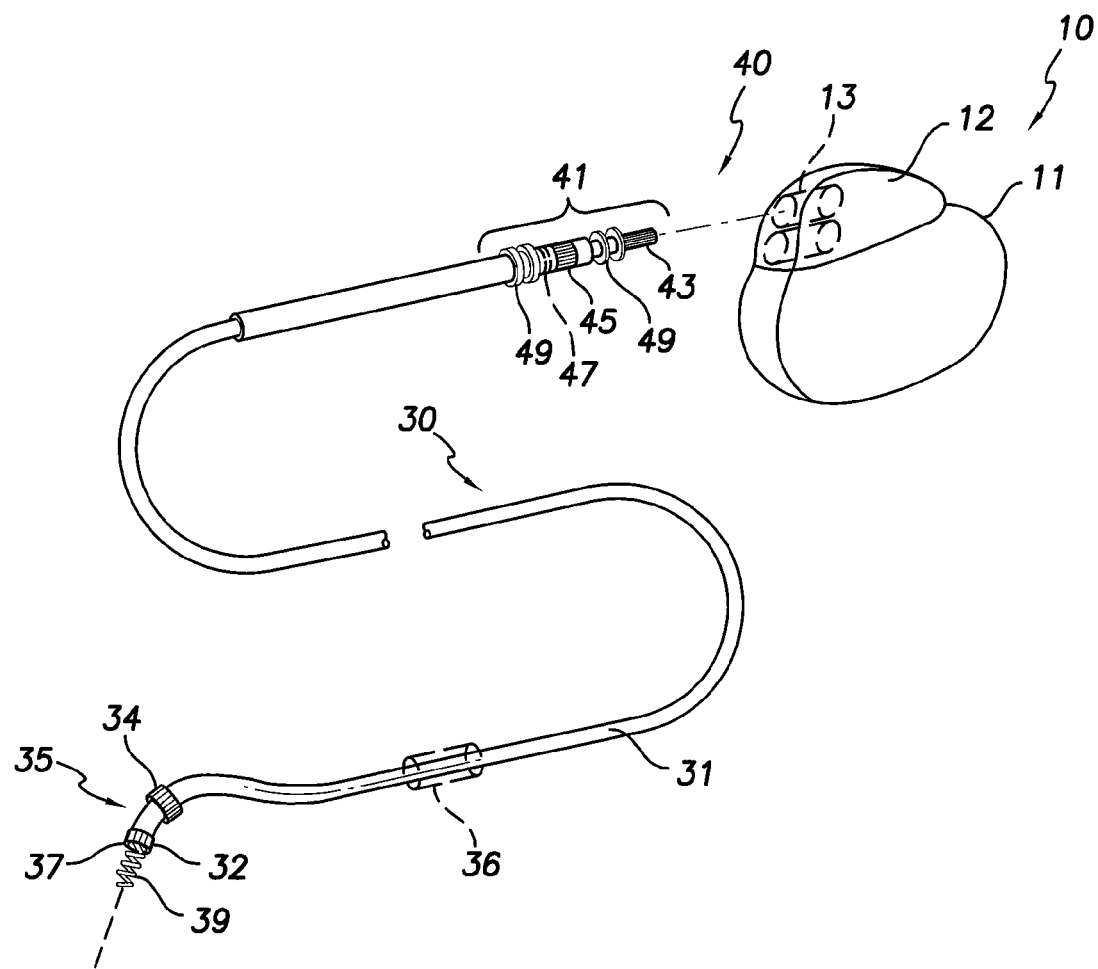
FIG. 2 is an isometric view of an implantable medical lead and a pulse generator for connection thereto.

For an overview discussion regarding an embodiment of an implantable lead, reference is made to FIG. 2, which is an isometric view of such a lead 30 and a pulse generator 10 for connection thereto. As shown in FIG. 2, the pulse generator 10, which may be, for example, a neurostimulator, pacemaker, defibrillator or ICD, may include a housing 11 and a header 12. The housing 11 may enclose the electrical components of the pulse generator 10. The header 12 may be mounted on the housing 11 and may include lead receiving receptacles 13 for connecting one or more leads 30 to the pulse generator 10.

As illustrated in FIG. 2, in one embodiment, the lead 30 may include a proximal end 40, a distal end 35 and a tubular body 31 extending between the proximal and distal ends. The proximal end 40 may include a lead connective end 41 having a pin contact 43, a first ring contact 45, a second ring contact 47, which is optional, and sets of spaced-apart radially projecting seals 49. In other embodiments, the lead connective end 41 may include a greater or lesser number of contacts and may include the same or different types of seals. The lead connective end 41 may be received in one of the lead receiving receptacles 13 of the pulse generator 10 such that the contacts 43, 45, 47 electrically contact corresponding electrical terminals within the respective receptacle 13 and the seals 49 prevent the ingress of body fluids into the respective receptacle 13.

As depicted in FIG. 2, in one embodiment, the lead distal end 35 may include a distal tip 37, an anchor 39, a tip electrode 32, and a ring electrode 34. The anchor 39 may be extendable from an orifice in the distal tip 37. The tip electrode 32 may form the distal tip 37 of the lead body 31, and the ring electrode 34 may extend about the circumference of the lead body 31 proximal of the tip electrode 32. In other embodiments, there may be a greater or lesser number of electrodes 32, 34 in similar or different configurations. Also, the anchor 39 may or may not have other configurations and may or may not also serve as an electrode.

As indicated in FIG. 2, the lead 30 may include an optional defibrillation coil 36, which may extend about the circumference of the lead body 31. The defibrillation coil 36 may be located proximal of the ring electrode 34.

In one embodiment, the tip electrode 32 may be in electrical communication with the pin contact 43 via electrical conductors, the ring electrode 34 may be in electrical communication with the ring contact 45 via other electrical conductors, and the defibrillation coil 36 may be in electrical communication with the second ring contact 47 via yet other conductors. The various conductors may extend through the lead body 31.

But for the novel circuitry and methods discussed herein, the conductors of the lead could act as an antenna in the radio frequency RF field of an MRI. As a result, current could be induced in the conductors, causing the conductors and the electrodes connected thereto to stimulate and/or heat and potentially damage the lead and/or tissue contacting the electrodes. Although the leads and methods disclosed herein may be applicable to various devices as discussed above, the following description is provided in the context of an implantable cardiac device and an implantable lead for such a device, such as described above with respect to FIGS. 1 and 2.

Within the context of an implantable cardiac device, connections to an implantable lead may be complicated. However, the connections may general include two main circuits, as illustrated in the schematic diagram of FIG. 3. The resistance depicted on the left represents the resistance seen by the device, including the patient, which may be, for example, 200-500 ohms.

A recharging circuit 50 may be employed to discharge a coupling capacitor 52 that is disposed in series with a pacing pulse from the pulse generator (not shown). During a pacing pulse, the coupling capacitor 52 charges, and thus needs to be discharged between pulses. Discharging of the coupling capacitor 52 may be accomplished in two phases. First, an active phase may employ a switching element 54, such as a metal-oxide-semiconductor field-effect transistor (MOSFET), to short the coupling capacitor 52 through the impedance of the patient, for example. Second, a passive phase may employ a resistor 54 with a value of 40 kΩ, for example, to maintain a relatively low resistance/impedance to fully discharge the coupling capacitor 52.

A sensing circuit 60 may be employed to sense intrinsic values from the patient, for example, to determine proper pacing therapy. The sensing circuit 60 may be in parallel with the recharging circuit 50, and may include an amplifier (not shown) with an input resistance on the order of 10 MΩ.

Figure 3:
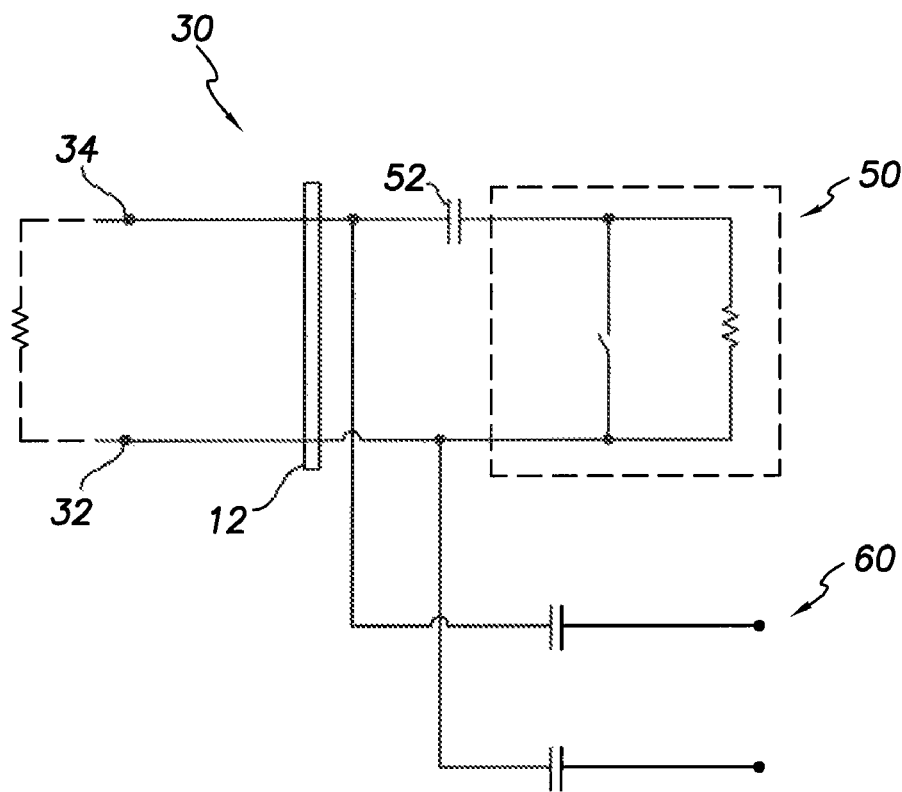
FIG. 3 is a schematic diagram illustrating circuits of an implantable stimulation device.

As illustrated in FIG. 3, the recharging circuit 50 and the sensing circuit 60 may be implemented in the pulse generator (not shown) upstream of the header 12 (shown schematically) that connects the lead, represented by the ring electrode 34 and the tip electrode 32, to the pulse generator. In general, electrical pacing pulses may be delivered from the pulse generator with the ring electrode 34 positive and the and the tip electrode 32. Pacing with the opposite polarity is typically not desirable as it may increase the pacing threshold.

The leads and methods described herein involve changing the impedance of the lead to reduce or even eliminate risks of stimulation and/or heating resulting from exposure to magnetic and/or electrical fields. It should be appreciated that a higher impedance of a lead will generally result in less induced current, other factors being equal. However, to maintain the integrity of at least the recharging circuit 50, any impedance added to the lead should not be too large. Too large of an impedance may undesirably inhibit discharging of the coupling capacitor 52, for example, by preventing the recharging circuit from completely discharging the coupling capacitor 52 between pacing pulses.

The sensing performed by the sensing circuit 60 is less likely to be adversely affected by added impedance because its input impedance may be relatively high. This is particularly the case as long as the added impedance is in on the order of tens of kilo-ohms or less, which may produce no significant impact on the sensing circuit 60.

Further, it may be undesirable to increase impedance of the lead for pacing purposes. First, the increased impedance may increase the capture threshold to such a degree that capture is reliable or perhaps not even possible. Second, the increased impedance may increase the necessary charge for pacing, perhaps to such a degree as to require a much larger battery voltage, which may ultimately reduce the longevity of the pulse generator.

Therefore, the leads and methods described herein involve an active solution, that is, actively changing the impedance of the lead. As described herein, the active changing of the impedance may be based on pacing signals, or may be based on signals having opposite polarity to pacing signals. As such, the leads described herein may include at least one active circuit element that is configured to change an impedance of the lead in response such signals.

Figure 4:
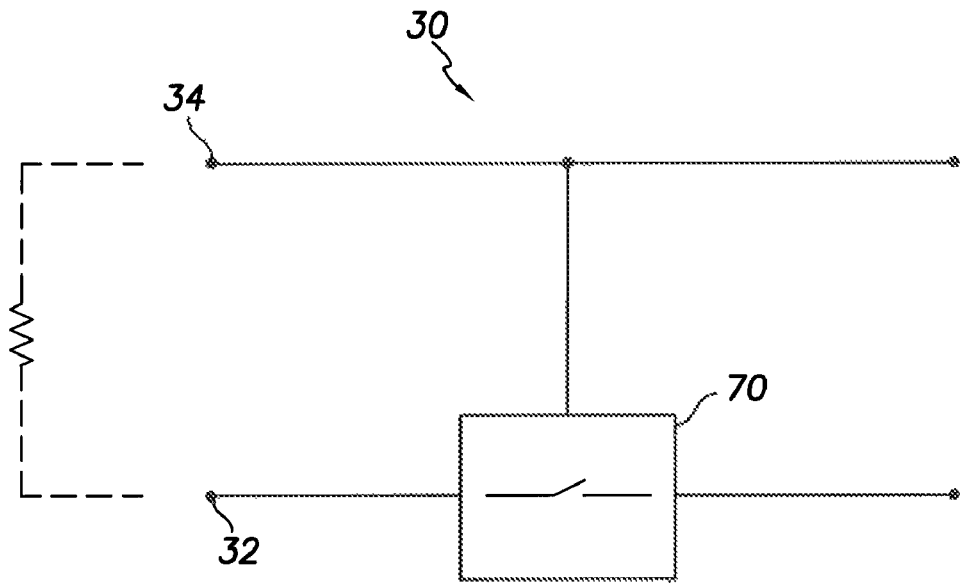
FIG. 4 is a simplified schematic diagram of an implantable medical lead including an active circuit element.

FIG. 4 is a simplified schematic diagram of an implantable medical lead 30 including an active circuit element 70. As shown, the active circuit element 70 may be in electrical communication with the ring electrode 34 and the tip electrode 32. In particular, the active circuit element 70 may be disposed proximate the distal tip of the lead, remote from the header of the pulse generator. Disposing the active circuit element 70 near the lead connective end, near the header, may result in significantly increased heating.

The active circuit element 70 may be configured to effectively open and close a circuit formed by the conductor of the lead connecting the ring electrode 34 and the tip electrode 32. Thus, the active circuit element 70 may comprise a switching element, and may switch from open to closed in response to pacing signals, or in response to signals having opposite polarity to pacing signals. As discussed above, a pacing signal is typically asserted by a positive voltage being applied between the ring electrode 34 and the tip electrode 32. Thus, a signal having opposite polarity may be asserted, for example, by a negative voltage being applied.

When the active circuit element 70 is open, the lead may have a relatively high impedance. When the active circuit element 70 is closed, the lead may have a relatively low impedance. Thus, the active circuit element 70 may change the impedance of the lead 30 in response to signals so that the lead 30 either has a relatively low impedance during pacing and a relatively high impedance otherwise, or has a relatively high impedance during exposure, for example, to MRI or radio frequency (RF) energy and a relatively low impedance otherwise.

Figure 5:
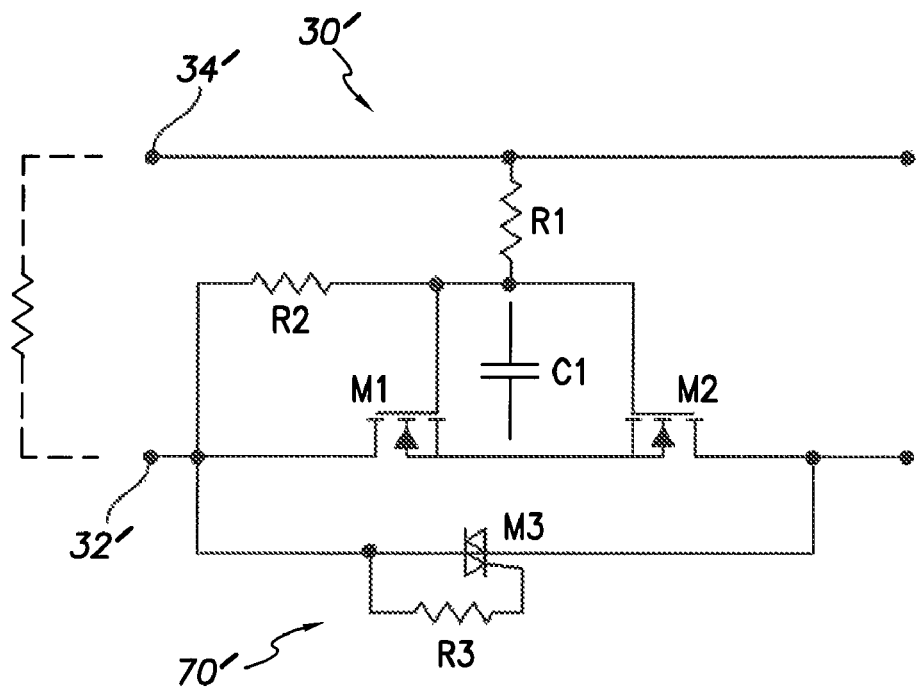
FIG. 5 is a schematic diagram of an implantable medical lead including two opposing MOSFETs according to one embodiment.

FIG. 5 is a schematic diagram of one embodiment of an implantable medical lead 30' including a tip electrode 32' and a ring electrode 34'. In this embodiment, an active circuit element 70' may comprise two opposing MOSFETs M1 and M2. The MOSFETs M1 and M2 may be N-channel MOSFETs and may be configured to effectively block radio frequency (RF) noise. The MOSFETs M1 and M2 may be arranged to block voltage in either direction. Various solutions described herein may provide a minimum of 1000Ω of impedance to reduce the potential effects of radio frequency noise on the lead, and therefore the device and the patient. An impedance of 1000Ω may be expected to reduce heating, for example, by more than 90 percent.

When the MOSFETs M1 and M2 are active, the impedance of the lead 30' may be relatively low, for example, on the order of 1Ω. The threshold voltages for the MOSFETs M1 and M2 should also be relatively low, such as 0.5V.

A first resistor R1 may be disposed between the ring electrode 34' and the MOSFETs M1 and M2. The value of the first resistor R1 may be selected so that no RF energy is transferred from the ring electrode 34' through capacitances to the gates of the MOSFETs M1 and M2.

In operation, the conductor of the lead is normally open as there is normally no voltage between the ring electrode 34' and the tip electrode 32'. In other words, MOSFETs M1 and M2 are normally open or off. During a pacing pulse/signal, a positive voltage may be applied between the ring electrode 34' and the tip electrode 32'. When this voltage is sufficiently high, for example, 1V, the MOSFET M1 will close (turn on) and will conduct with an impedance of, for example, 1Ω. In turn, the MOSFET M2 will be reverse biased and act like a diode with a maximum of, for example, 0.7V source-to-drain. If the voltage between the ring electrode 34' and the tip electrode 32' is sufficiently high, that is, above the threshold voltage ($V_{th}$) of MOSFET M2, the MOSFET M2 will close (turn on) and will conduct with an impedance of, for example, 1Ω. Thus, the pacing signal will trigger the MOSFETs M1 and M2 to create a relatively low-impedance path for the pacing pulse.

Optionally, a capacitor C1 may be disposed in parallel with the MOSFET M2 to aid in turning on the MOSFET M2. The capacitor C1 is depicted unconnected as an optional element.

However, it should be understood that the capacitor C1 may be connected to the MOSFET M2 in any suitable manner, such as source to gate.

A second resistor R2 may be disposed in parallel with the MOSFET M1 to allow the MOSFET M1 to become partially active to reduce the impedance of the lead 30'. The value of the second resistor R2 may be selected similarly to the selection of the value of the first resistor R1. Allowing the MOSFET M1 to become partially active may be advantageous, for example, in situations in which the ring electrode 34' is damaged and pacing ring electrode to tip electrode is not possible. The pulse generator may compensate for such damage by unipolar pacing, that is, applying a voltage between the housing or can of the pulse generator and the tip electrode 32'. The reduction in impedance provided by the partial activation of the MOSFET M1 may not be sufficient in some instances to provide pacing without increasing the pacing amplitude and/or an increase in the capture threshold.

The lead 30' may also include a protection circuit 80', for example, to protect the MOSFETs M1 and M2 from excessive voltages, such as that occur during external or internal defibrillation. The protection circuit 80' may comprise a thyristor device M3, such as a symmetrical trigger diode (DIAC (diode for alternating current) or SDIAC (silicon diode for alternating current)), or triac, that conducts current only after its breakdown or breakover voltage has been momentarily exceeded and continues to conduct until the current flow drops below its holding current value.

A third resistor R3 may be disposed in parallel with the thyristor device M3. The value of the third resistor R3 may be selected so that the thyristor device M3 is active if the voltage across the MOSFETs M1 and M2 is excessive, for example, greater than 12V. If, for example, the tip electrode 32' becomes a high voltage terminal, the voltage formed across the MOSFETs M1 and M2 will cause current to flow through R3. When the current flowing through R3 is great enough to cause the breakdown voltage of the thyristor device M3 to be exceeded, the thyristor device M3 will turn on and conduct, thereby shunting potentially damaging current around the MOSFETs M1 and M2. The third resistor R3 also may provide a path for sensing to allow for sensing when the MOSFETs M1 and M2 are off. As gate-to-terminal in the thyristor device M3 may be, for example, around 20 ohms, an open circuit may otherwise result with the MOSFETs M1 and M2 off.

An alternate embodiment not separately illustrated may be similar to the embodiment shown in FIG. 5, without the second and third resistors R2 and R3 or the thyristor device M3. In such an alternative embodiment, the MOSFETs M1 and M2 may be depletion mode MOSFETs. As depletion mode MOSFETs are normally closed (turned on), the lead would normally have its relatively low impedance value and no change in impedance would be needed for pacing. However, during exposure to RF energy, signals or noise, such as MRI, a negative voltage would be applied to the gates of the depletion mode MOSFETs to change the impedance of the lead to its relatively high value. The negative voltage may be provided, for example, from the battery of the pulse generator through suitable switches. As discussed above, this negative voltage or signal may have opposite polarity to the pacing signals employed by the device.

Figure 6:
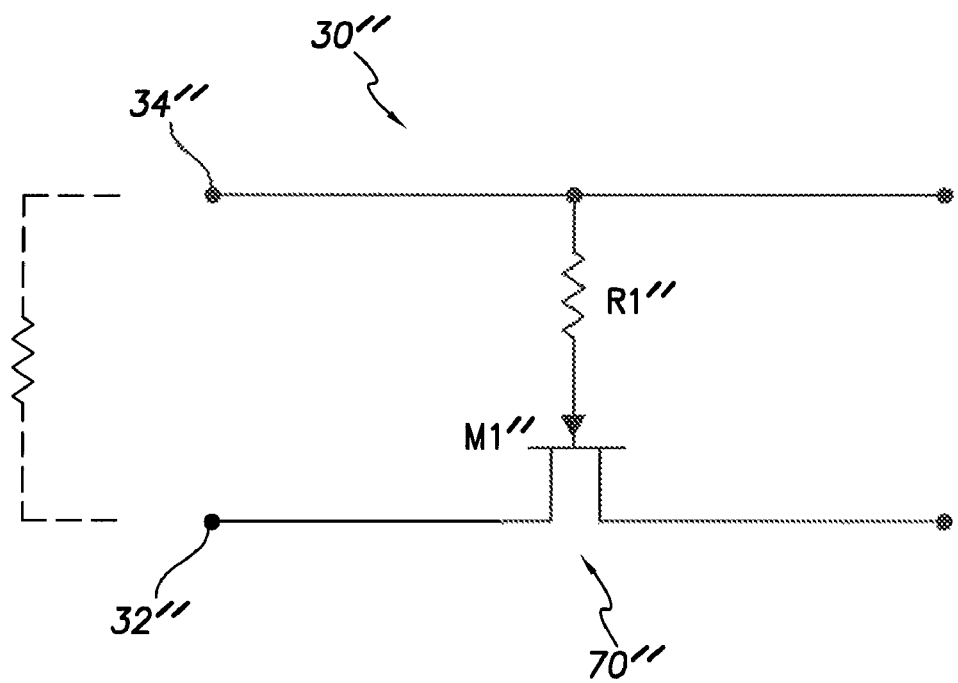
FIG. 6 is a schematic diagram of an implantable medical lead including a JFET according to another embodiment.

FIG. 6 is a schematic diagram of another embodiment of an implantable medical lead 30" including a tip electrode 32" and a ring electrode 34". In this embodiment, an active circuit element 70" may comprise a junction gate field-effect transistor (JFET) M1". As described above, a first resistor R1" may be disposed between the ring electrode 34" and the JFET M1".

As the JFET M1" is a depletion mode device (using PN junctions rather than oxide gate layers), its operation may be as described above, being normally closed (turned on) to provide a relatively low-impedance mode for pacing, for example, and opened (turned off) by a signal, such as an opposite polarity signal, to provide a relatively high-impedance mode for MRI, for example.

Figure 7:
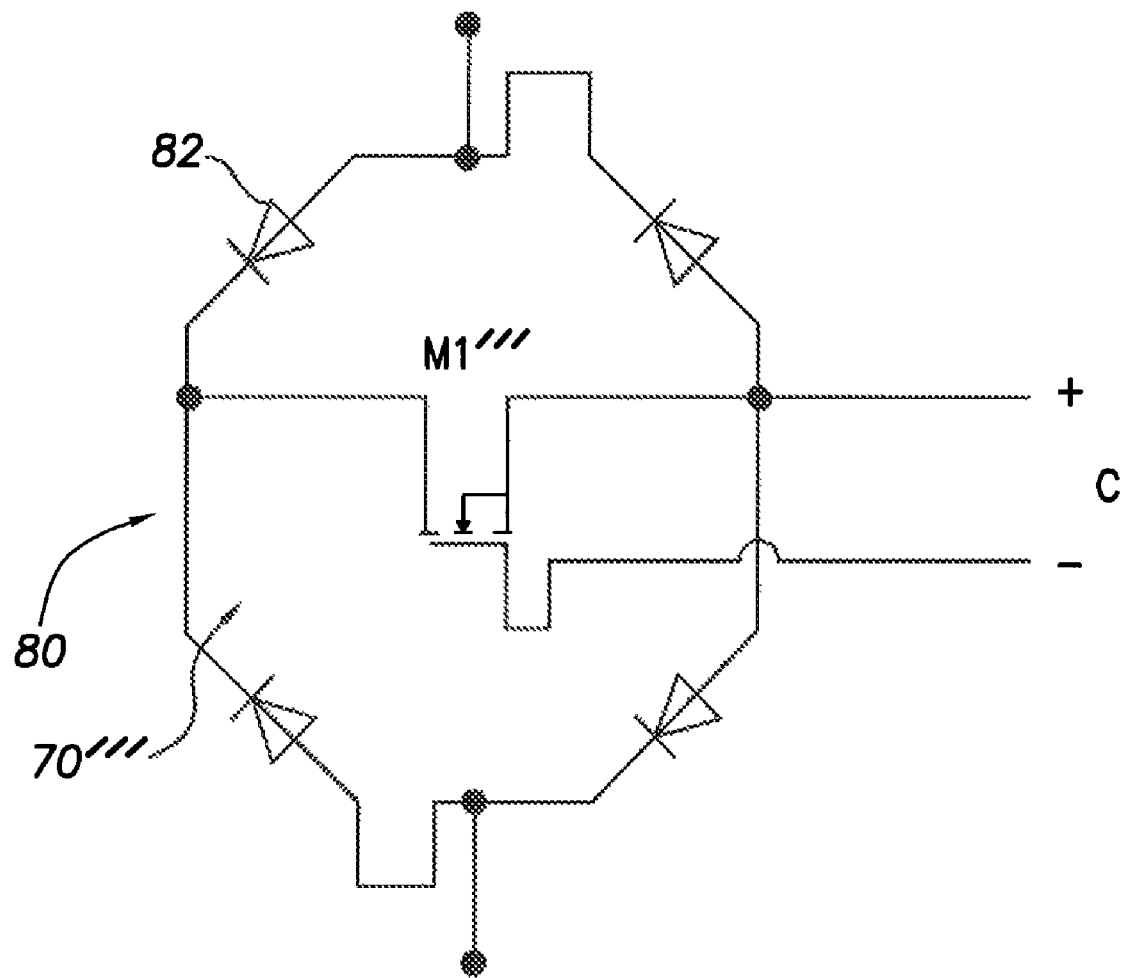
FIGS. 7-9 are schematic diagrams of examples of circuits including an active circuit element for use in an implantable medical lead according to various embodiments.
Figure 8:
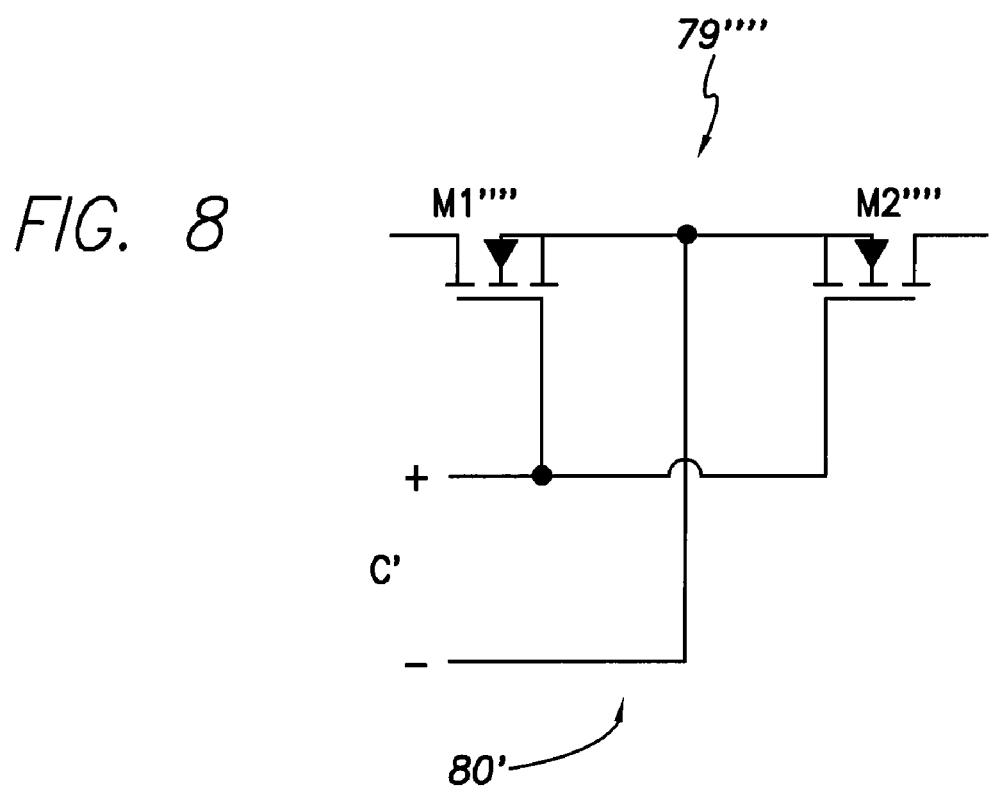
Figure 9:
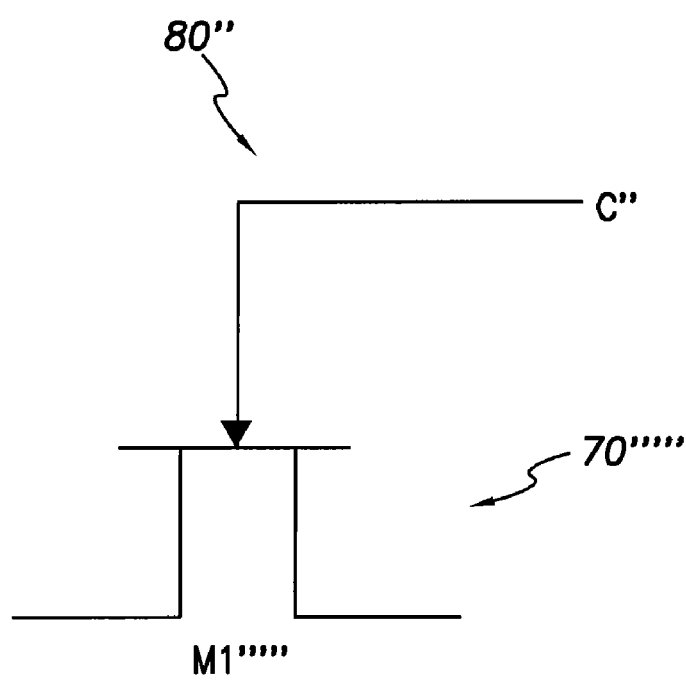

Further examples of embodiments of circuits including active circuit elements that may be employed in an implantable medical lead are illustrated in FIGS. 7-9. As discussed above, each of these circuits may be incorporated into a medical lead so as to be disposed between an implantable medical device and an electrode of the lead when the lead is connected to the device. As described above, the active circuit elements may be configured to change the impedance of the lead in response to a pacing signal or a signal having opposite polarity to a pacing signal.

Alternatively, as depicted in FIGS. 7-9, the active circuit elements may be configured to change the impedance of the lead in response to a separate control signal from a controller. It should be understood that the controller may be any suitable device, such as a microprocessor or the like, that is configured to provide appropriate control as described herein. It should also be understood that the controller may provide the control signal directly or indirectly, for example, by controlling another device, such as a voltage source.

FIG. 7 is a schematic diagram illustrating a circuit 80 including an active circuit element 70'''. As shown, the active circuit element 70''' may comprise a MOSFET M1''', which may be suitably connected to receive signals from a control C. The control signals may turn on the MOSFET M1''' to allow normal conduction to the electrode of the lead, for example, of pacing pulses, and may turn off the MOSFET M1''' to increase impedance of the lead. As shown, the circuit 80 may include a diode bridge 82, which may prevents signals from reaching the electrode without the MOSFET M1''' turned on.

FIG. 8 is a schematic diagram illustrating another circuit 80' including an active circuit element 70''''. As shown, the active circuit element 70'''' may comprise a first MOSFET M1'''' and a second MOSFET M2'''', each of which may be suitably connected to receive signals from a control C'. The control signals may turn on and off the MOSFETs M1'''' and M2'''' to switch between normal conduction to the electrode and increase impedance of the lead.

FIG. 9 is a schematic diagram illustrating another circuit 80'' including an active circuit element 70'''''. As shown, the active circuit element 70''''' may comprise a JFET M1''''', which may be suitably connected to receive signals from a control C'. The control signals may turn on and off the JFET M1''''' to switch between normal conduction to the electrode and increase impedance of the lead.

Component selection may be important for various embodiments described herein. For example, parasitic capacitances in the MOSFETs M1 and M2 and/or the thyristor device M3 may undesirably allow RF energy to bypass such elements if the parasitic capacitances are not controlled or minimized. For example, such capacitances may be on the order of 1 pF. At 64 MHz, for example, a 1 pF capacitor has an equivalent series resistance (ESR) of approximately 2.5 kΩ. At 128 MHz, a 1 pF capacitor has an equivalent series resistance (ESR) of approximately 1.25 kΩ.

In some implementations, pacing amplitudes may need to be increased to compensate for the threshold voltage of the active circuit element(s), such as the opposing MOSFETs described above, disposed in series with the pacing pulse. However, capture threshold may not increase. For example, if a nominal capture threshold for a patient is 0.5V at 0.5 ms, the amplitude may not be sufficient to activate the active circuit element(s), and the lead may undesirably present relatively high impedance for pacing. However, increasing the amplitude to 1.5V, with a threshold of 0.5V, may activate the opposing MOSFETs to allow the full 1.5V pulse to pass.

Increasing pacing amplitude may not be necessary in some implementations though. For example, if capture threshold for a patient is 2.0V at 0.5 ms, the amplitude may be sufficient to activate the active circuit element(s), and the lead may present relatively low impedance for pacing.

Pacing pulse duration may also need to be increased for some implementations, for example, to compensate for turn on times of the active circuit element(s), such as the opposing MOSFETs described above.

As discussed herein, the approach of including one or more active circuit elements in a lead may be used to reduce or even eliminate the adverse effects of currents that would otherwise be induced in leads exposed to magnetic and/or electric fields. In general, the active circuit element(s) may effectively electronically open and close a circuit comprising the lead. It should be understood that the approach described herein may be combined with the approaches designed to reduce the effect of undesired heating and/or induced currents in leads.

While other approaches may not satisfactorily reduce or eliminate both heating and induced currents, the leads and methods described herein may address both problems simultaneously. Induced currents may have a frequency spectrum similar to pacing pulses, whereas heating energy may be generated at 64 Mhz or 128 MHz. Any solution directed at reducing or removing both heating and induced current thus needs to work at 64 Mhz or 128 MHz as well as in the kilohertz range to be effective. The leads and method described herein are not frequency dependent, and thus operate effectively for both problems.

It should be understood that the different embodiments described herein are not mutually exclusive or exhaustive of the embodiments contemplated. In particular, any of the features discussed with respect to one of the embodiments may be employed in combination with any of the features discussed with respect to other embodiments. Thus, although the present invention has been described with reference to preferred embodiments, persons skilled in the art will recognize that changes may be made in form and detail without departing from the spirit and scope of the invention.

What is claimed is:

1. An implantable medical lead for coupling to an implantable pulse generator and configured for improved safety, the lead comprising:
    a lead body including a distal portion with a first electrode and a proximal portion with a lead connector, the lead body having at least one conductor coupling the first electrode to a first connector contact; and
    at least one active circuit element contained within the lead body and in electrical communication with the first electrode and coupled in series between the conductor and the electrode, the at least one active circuit element configured to change an impedance of the lead.

2. The lead of claim 1, wherein the at least one active circuit element is configured to change an impedance of the lead in response to at least one of a pacing signal and a signal having opposite polarity to a pacing signal.

3. The lead of claim 1, further comprising a second electrode in electrical communication with the first electrode; wherein the at least one active circuit element is disposed in series between the first and second electrodes.

4. The lead of claim 3, further comprising at least one resistor disposed between first electrode and the active circuit element.

5. The lead of claim 1, wherein the at least one active circuit element comprises at least one switching element.

6. The lead of claim 5, wherein the at least one switching element comprises a depletion mode device.

7. The lead of claim 5, wherein the at least one switching element comprises a JFET.

8. The lead of claim 5, wherein the at least one switching element comprises at least one MOSFET.

9. The lead of claim 8, wherein the at least one MOSFET is a depletion mode MOSFET.

10. The lead of claim 8, further comprising a protection circuit disposed in parallel with the at least one MOSFET.

11. The lead of claim 10, wherein the protection circuit comprises a thyristor device.

12. The lead of claim 11, wherein the protection circuit further comprises at least one resistor in parallel with the thyristor device.

13. The lead of claim 8, wherein the at least one switching element comprises two opposing MOSFETs.

14. The lead of claim 13, wherein the two opposing MOSFETs are depletion mode MOSFETs.

15. The lead of claim 13, further comprising a protection circuit disposed in parallel with the two opposing MOSFETs.

16. The lead of claim 15, wherein the protection circuit comprises a thyristor device.

17. The lead of claim 16, wherein the protection circuit further comprises at least one resistor in parallel with the thyristor device.

18. A method of using an implantable medical lead for improved safety, the method comprising:
    delivering a control signal to an active circuit element coupled within a body of the lead to change an impedance of an implantable medical lead from a relatively high impedance to a relatively low impedance, wherein the control signal comprises a pacing signal.

19. A method of using an implantable medical lead for improved safety, the method comprising:
    delivering a control signal to an active circuit element coupled within a body of the lead to change an impedance of an implantable medical lead from a relatively low impedance to a relatively high impedance, wherein the control signal comprises a signal having opposite polarity to a pacing signal.

* * * * *